United States Patent [19]

Vance

[11] Patent Number: 4,700,180

[45] Date of Patent: Oct. 13, 1987

[54] APPARATUS TO INDICATE WHEN A PATIENT HAS EVACUATED A BED

[76] Inventor: Dwight A. Vance, 101 S. Joshua, Broken Arrow, Okla. 74012

[21] Appl. No.: 878,502

[22] Filed: Jun. 23, 1986

Related U.S. Application Data

[63] Continuation of Ser. No. 491,355, May 4, 1983, abandoned.

[51] Int. Cl.[4] .............................................. G08B 23/00
[52] U.S. Cl. .................................. 340/573; 340/384 E; 340/667
[58] Field of Search ............... 340/573, 384 E, 384 R, 340/666, 667, 668, 686, 512

[56] References Cited

U.S. PATENT DOCUMENTS

| | | | |
|---|---|---|---|
| 4,206,448 | 6/1980 | Davis | 340/384 E |
| 4,242,672 | 12/1980 | Gault | 340/667 X |
| 4,280,123 | 7/1981 | Right et al. | 340/384 E |
| 4,295,133 | 10/1981 | Vance | 340/573 |
| 4,359,726 | 11/1982 | Lewiner et al. | 340/573 X |
| 4,438,771 | 3/1984 | Friesen et al. | 340/573 X |

Primary Examiner—James L. Rowland
Assistant Examiner—Jeffery A. Hofsass
Attorney, Agent, or Firm—Head & Johnson

[57] ABSTRACT

A monitoring system for a bed patient comprising a binary signal generating means to provide a first signal when the patient is in the bed and a second signal when the patient is out of the bed. An alternating electrical power supply passes to a frequency divider so that electrical pulses of selected time spacing are derived by means of which time can be measured. These pulses go to a signal delay means with adjustments possible for any selected delay and then to a latch means. Alarm control means are provided responsive to the operation of the latch for controlling the nature of the alarm signal. The alarm control means alternately provides electrical alarm signals of various sorts, such as a single short pulse or an indefinitely long pulse or an alternating signal. Each of these could separately control a visual or audible alarm means. This invention is compatible with normal call equipment and alarms in hospitals.

2 Claims, 2 Drawing Figures

APPARATUS TO INDICATE WHEN A PATIENT HAS EVACUATED A BED

This is a continuation application of Ser. No. 491,355, filed May 4, 1983 abandoned.

CROSS-REFERENCE TO RELATED PATENTS

This application is related to my two U.S. Pat. Nos. 4,179,692 and 4,295,133, issued respectively Dec. 18, 1979 and Oct. 13, 1981. Both are entitled: "APPARATUS TO INDICATE WHEN A PATIENT HAS EVACUATED A BED OR DEMONSTRATES A RESTLESS CONDITION".

BACKGROUND OF THE INVENTION 1. 1. Field of the Invention

This invention lies in the field of hospital instrumentation. More particularly, it lies in the field of monitoring the presence or absence of a patient from a bed protected or monitored by this equipment.

2. Description of the Prior Art

In the prior art, instruments have been provided which monitor the presence or absence of a patient within a bed. Reference has been made to my two U.S. Pat. Nos. 4,179,692 and 4,295,133. I have found in operation of the previous styles of instruments that the nature or character of the alarm signal and control of the delay time between the switching means and the alarm, denoting the presence or absence of the patient in a bed, can be very important.

SUMMARY OF THE INVENTION

It is a primary object of this invention to provide a patient monitoring system for notifying the nursing staff whenever a patient, having the monitoring system, attempts to leave his bed.

It is a still further object of this invention to provide a monitoring system in which the alarm signal itself can be varied in nature, so as to provide a signal of selected character, which can be indicative to the nurses of this particular monitoring system also allowing compatibility with a variety of nurse call systems.

These and other objects and the limitations of the prior art are overcome in this invention by providing a binary signal generating means, or a switch means, which is placed in the bed under the patient, such that when the patient is lying down in the bed on said switch means, an electrical circuit will be closed; and when the patient is not resting on said switch means, that is, when he is sitting on the edge of the bed or is out of the bed, the switch means will be open and that switch condition will then trigger a latch to provide the alarm.

Time signals are taken from an electrical alternating power source of appropriate frequency and are delivered to a frequency divider which will divide the sixty cycles by sixty to provide a signal pulse each second, for example. Digital counting delay means are provided for monitoring the bed switch means and the frequency divider to introduce a time delay of a selected number of seconds or minutes. Switch means are provided on the output of the counter to select any time delay within the scope of the instrument, so as to compensate for patient activity or restlessness.

The latch is a flip-flop of commercial design and is designed to monitor the signal on the output line from the delay circuit; and when this voltage goes positive, an appropriate signal is placed on the set terminal of the latch, and appropriate voltages are then applied internally to the two output terminals—the so-called Q and $\overline{Q}$ terminals. Both the Q and $\overline{Q}$ terminals are utilized in conjunction with other control elements, such as a monostable flip-flop and an astable flip-flop. The monostable flip-flop puts out a single pulse of selected time length, which may last for one or more seconds, for example, and then cuts off the alarm signal. The astable flip-flop provides a continuing series of short pulses, and these continue until the latch is reset. Also, the output of the latch itself provides a signal that goes positive and remains positive indefinitely until the latch is reset.

The outputs of the latch, the monostable flip-flop and astable flip-flop go through circuit isolators to a multipoint 38 so that the nature of the alarm signal can be selected alternatively to one of three types—such as, for example, a single medium long pulse or a continuing long pulse or a continuing series of short pulses. This helps assure compatibility with a variety of nurse call systems. These three types of signals, from which are chosen the operating alarm signal, control a relay which provides a selected voltage on a pair of conductors that go from the patient's room to the nursing station so that the alarm of whatever nature, be it audible or visual, will be called immediately to the attention of the nurses.

Separate alarms such as an audible oscillator signal or a light 52 can be provided on the face of the instrument so that the fact that the latch is closed will be immediately evident to nursing personnel in the room.

Means are provided at the bed including a flip-flop so that by closing a switch 66 at the bed, the alarm signal can be nullified. Also, a reset switch 68 is provided that will reset the latch and turn off all alarms after the patient has been put back in bed and the switch under the patient is then closed,. An automatic reset is provided should switch 68 not be reset.

I have found a very satisfactory type of bed switch means which is in the form of a mat of selected length and width. It is made as a sandwich of several different conducting and insulating plastic sheets. The central body of the mat comprises a thin sheet of compressible insulating material which can be a small fraction of an inch in thickness. At least one opening is provided in the center of the layer. Insulating plastic films having a coating on one face of conducting powder or metal, are provided, one on top of the central sheet, and one on the bottom of the central sheet with the conducting coatings facing inwardly. Electrical conductors are attached to each of the two conducting layers. When this mat is cemented together and placed.in the bed and the weight of the patient is placed on the mat, the central compressible insulating layer is squeezed under the weight of the patient; and in the opening provided, the two conducting layers can be brought together to close the circuit. This comprises the switch which indicates when the patient is in the bed by having that circuit closed; and when the patient is up off the mattress, then the springiness of that central compressible material will separate the two conducting layers, and the circuit will open. This opening of the circuit initiates the delay, the latch, and the alarm signals.

BRIEF DESCRIPTION OF THE DRAWINGS

These and other objects and advantages of this invention and a better understanding of the principles and details of the invention will be evident from the following description, taken in conjunction with the appended drawings in which.

DESCRIPTION OF THE PREFERRED EMBODIMENT

Figure 1:
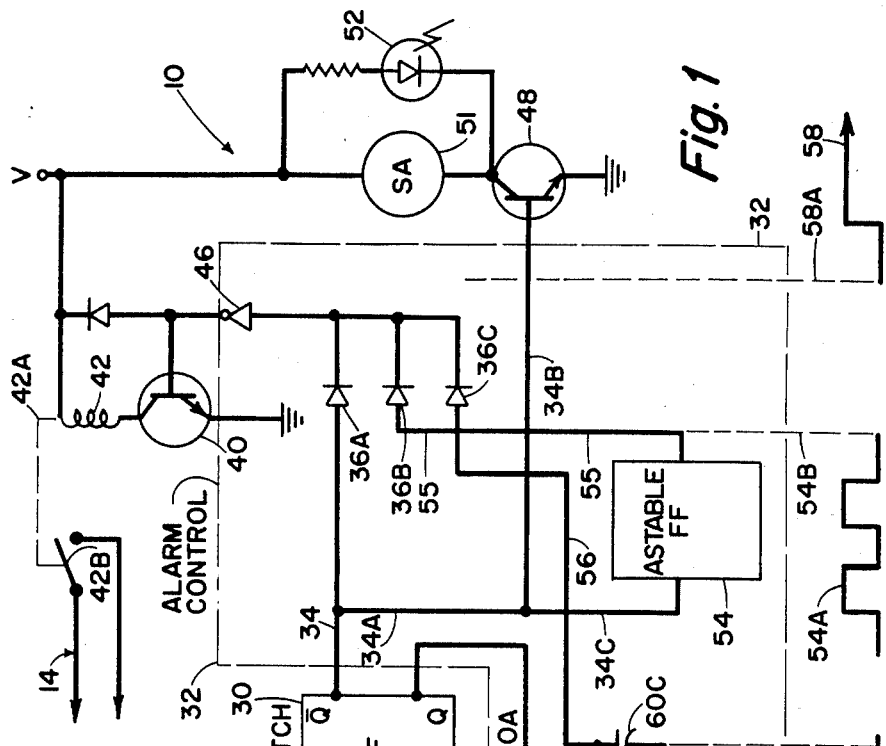
FIG. 1 is a schematic diagram of the complete instrument, including the mat, the timing control, the latch, and the alarm control means.

Referring now to the drawings, there is shown in schematic form one embodiment of this invention. There are two principal parts—the electronic circuits for delay and control of the alarm, and a separate sensor, bed switch, or binary signal generating means which is used to provide the control signal that initiates the latch and the alarm. The numeral 10 indicates generally the electronic circuitry. The numeral 12 indicates the sensor or the binary signal generating means which is used to generate a first signal when the mat is placed in the bed and the patient is resting on the mat, and to provide a different kind of signal when the patient is not resting on the mat.

Referring now to FIG. 1, the upper left-hand corner shows the binary signal generating means 12 which is also called a mat or a sensor. This binary signal generating means acts like a switch 16 that is closed when a patient has his weight resting on the mat, and that is open when there is no patient resting on the mat.

Operating power for the electronics is provided by a power supply (not shown) which can be conventional in all respects and will put a selected dc voltage V at selected points in the circuit. The precise value of voltage depends on the type of electronic devices, integrated circuits, etc. Part of the ac power supply is passed through leads 17, shown, to the frequency divider 20. This provides output pulses of a selected frequency, such as one per second, by counting down the sixty Hz; and for each sixty alternations a single output pulse is provided, for example.

The output signal pulses from the frequency divider 20 go by lead 22 to a binary counter type time delay means 24. A second input to the counter goes from the switch 16 in the mat and responsive to the signal on 18, that is, whether it is grounded or not, controls the counter which then begins to count the number of pulses put out by the frequency divider. A selector switch 25 on the output of the counter delay means 24 selects a delay period of a certain number of seconds, and so on. The purpose of the delay is to avoid sounding the alarm when there is just a momentary changing of the switch 16. For example, a restless patient may momentarily lift himself up from the mattress, in which case the switch 16 will open. In order not to sound the alarm for each one of these momentary openings, the delay device 24 is utilized to pick out those signals which have been semi-continuous for a period of selected length.

If the switch 16 remains open longer than the delay period, then an appropriate voltage is placed on the lead 26 that goes to the latch. The inverter 27 provides the proper voltage to set the latch at the terminal S. When the latch 30 is set, appropriate voltages appear on the Q and $\overline{Q}$ terminals of the output. Once the flip-flop 30 is latched, then it stays in that condition until an appropriate voltage is placed on the terminal R, which is the reset terminal. When the latch is set, the Q terminal becomes positive or high, and the $\overline{Q}$ terminal becomes low or zero.

The dashed box 32 encloses a group of electronic elements which comprise means for forming an alarm signal of selected shape or character. The signal on line 34 goes by line 34A and 34B to a transistor 48 which amplifies the signal on 34 and provides an operating voltage to the sonic alarm 51 and to the visual alarm 52 which can be a light emitting diode, for example. The signal on 34 also goes by way of 34A and 34C to astable flip-flop 54. This type of flip-flop circuit puts out a signal at its output terminal, line 55, to which the dashed line, 54B is drawn. The output signal 54A is shown as a series of square pulses of selected duration which goes on indefinitely as long as the latch is closed.

The signal on the Q output of the latch 30 goes by lead 30A to a monostable flip-flop 60. This puts out a signal as shown and identified as 60A. This is a single square pulse of selected length, the length of which is varied by tuning the capacitor 60C and is connected to that capacitor by dash lines 60B. Incidentally, the signal on lead 34B going to the transistor 48 is shown by the dashed line 58A as a long, continuing signal 58. This indicates the type of signal presented to the sonic alarm 51 and the visual alarm 52.

Alarm signals to relay 42 can be selected by way of removing diodes. For example, (A) by removing diodes 36b and 36c a continuous alarm will be on relay 42; (B) by removing diodes 36a and 36c a pulsed alarm may be placed on relay 42; (C) by removing diodess 36a and 36b, one pulse of short duration will be placed on relay 42. A suitable switch for selecting the appropriate relay signal can be used.

The switch 66 attached across the set terminal of the hold flip-flop 62, when closed, sets the flip-flop and turns on the indicator 62A. After the patient is replaced in the bed and the switch 16 of the mat is again closed, then the reset switch 68 can be closed momentarily to reset the hold flip-flop 62, turn off all the alarms, and put the instrument back into a monitoring condition.

If switch 68 is not reset manually, an automatic reset is provided for the hold flip-flop 62. To prevent false triggering, as may be experienced when removing someone from a bed and switch 16 is closing and opening, a time delay is incorporated of approximately 10 seconds. Operation is as follows: Closing of switch 16 causes the output of inverter I-1 to go positive charging C10 through resistor R-23. This creates a time constant. When voltage reaches a sufficient amount on C-10 to cause the output of I-2 to go to ground momentarily grounding C-8 and placing a momentary grounding pulse at the junction of R-21, C-8 and Reset R of hold flip-flop 62. This resets hold flip-flop 62 thus arming the system by removing the hold signal through D-24 from the counter delay.

In the event switch 16 is opened before the 10 second delay, D-32 will discharge C-10 quickly. This prevents an error from occurring forcing C-10 to always start charging at zero voltage.

The numeral 14 indicates the two conductors that go to the nurses' station so that when the switch 42B is closed by means 42A from the relay 42, appropriate signalling means at the nurses' station will be provided.

Figure 2:
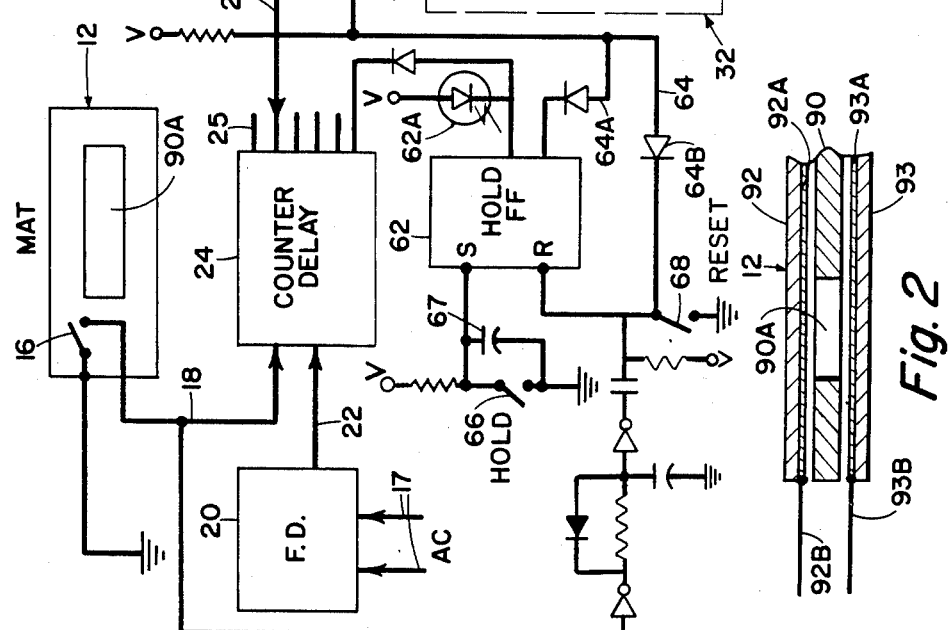
FIG. 2 is a cross-sectional view of the construction of the bed switch or mat.

Referring now to FIG. 2, there is shown in cross-section a portion of the mat 12 made up of three principal layers of material—a central layer 90 of selected length, width, and shape, with at least one opening 90A in the central portion. Of course, more than a single opening can be provided of lesser size, depending on the particular conditions.

This central layer 90 is covered by two plastic layers 92 and 93 which have had conducting material applied to one of their surfaces. This can be a thin metal film, such as provided by evaporation or sputtering of appropriate materials, or can be a conducting paint of some sort. The two conducting layers 92A and 93A face each other and are separated by the insulating material 90. Thus, when there is no weight on the mat 12, the two conducting layers will not touch, and two leads 92B and 93B can be provided. However, when this mat is placed in the bed and the patient is resting on the mat, the weight of the patient will compress the central layer 90 to a thinner dimension; and through the central opening 90A, the two conducting layers 92A and 93A can be pressed together to touch each other and close the circuit of switch 16.

While the invention has been described with a certain degree of particularity, it is manifest that many changes may be made in the details of construction and the arrangement of components without departing from the spirit and scope of this disclosure. It is understood that the invention is not limited to the exemplified embodiments set forth herein but is to be limited only by the scope of the attached claim or claims, including the full range of equivalency to which each element thereof is entitled.

What is claimed is:

1. A monitoring system for a bed patient, comprising:
    (a) binary signal generating means (BSGM) adapted to provide a first signal when said patient is in the bed, and a second signal when said patient is out of said bed, the BSGM being in the form of switch means in a mat placed under said patient in said bed adapted to change from a first operating position to a second operating position responsive to the weight of said body on said mat in said bed;
    (b) a frequency divider means for producing signal pulses at selected intervals of time;
    (c) signal delay means responsive to said frequency divider means and said BSGM;
    (d) latch means responsive to said signal delay means;
    (e) alarm control means responsive to said latch means including means for selecting the nature of the alarm signal;
    (f) alarm signal means;
    (g) a time delayed hold flip-flop circuit means to reset said latch and provide for automatic resetting;
    (h) said alarm control means including selectably (1) an astable flip-flop which provides a signal in the form of a series of square wave voltage pulses of selected duration as long as said latch means is closed, (2) a monostable flip-flop which provides a signal in the form of a single square wave voltage pulse of selectable length and (3) diode means connected to said latch means which provides a signal in the form of a continuous voltage signal existing until said latch is reset; and
    (i) means to select one of said voltage signals for application to said alarm signal means.

2. The monitoring system as in claim 1 in which said switch means comprises a mat, which comprises:
    (a) a thin sheet of compressible insulting material (CIM) of selected thickness, shape and size;
    (b) at least one opening of selected shape and size in the central portion of said sheet of insulation;
    (c) a first and a second sheet of flexible insulating material having one face covered with a thin sheet of flexible electrical conducting material;
    (d) said first sheet placed against one face of said sheet of CIM with said thin sheet of flexible conducting material in contact with said CIM, and said second sheet similarly placed in contact with the other face of said CIM: and
    (e) a first and a second electrical conductor attached one to each of said conducting layers;
    whereby when the weight of a body is placed on said mat, the CIM will compress in the vicinity of said at least one opening and will permit said two conducting material layers to touch and close the circuit between said two conductors.

* * * * *